(12) United States Patent
Rührnschopf et al.

(10) Patent No.: US 7,760,855 B2
(45) Date of Patent: Jul. 20, 2010

(54) METHOD FOR SCATTERED RADIATION CORRECTION

(75) Inventors: Ernst-Peter Rührnschopf, Erlangen (DE); Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 11/906,068

(22) Filed: Sep. 28, 2007

(65) Prior Publication Data

US 2008/0095313 A1 Apr. 24, 2008

(30) Foreign Application Priority Data

Sep. 29, 2006 (DE) .................. 10 2006 046 732

(51) Int. Cl.
*G01N 23/201* (2006.01)
(52) U.S. Cl. ........................ 378/87; 378/98.4
(58) Field of Classification Search ............... 378/98.4, 378/87, 62, 86, 97, 108
See application file for complete search history.

(56) References Cited

U.S. PATENT DOCUMENTS 6,104,777 A * 8/2000 Darboux et al. ............... 378/62

FOREIGN PATENT DOCUMENTS

DE 2642846 A1 3/1978
DE 102004029010 A1 1/2006

OTHER PUBLICATIONS

Dean A. Hinshaw and James T. Dobbins III; "Recent progress in noise reduction and scatter correction in dual-energy imaging"; Proc. SPIE; 1995; vol. 2432; pp. 134-142.
Richard J. Warp, James T. Dobbins III; "Quantitative evaluation of noise reduction strategies in dual-energy imaging"; Med. Phys. 30 (2), Feb. 2003; pp. 190-198.
Carey E. Floyd, Jr., Jay A. Baker, Joseph Y. Lo, and Carl E. Ravin; "Posterior Beam-Stop Method for Scatter Fraction Measurement in Digital Radiography"; Investigative Radiology; Feb. 1992; vol. 27; pp. 119-123.
M. Zellerhoff, B. Scholz, E.-P. Rührnschopf and T. Brunner; "Low contrast 3D-reconstruction from C-arm data"; Proceedings of SPIE Medical Imaging; 2005; pp. 646-655; vol. 5745.
Press et al., "Numerical Recipies—The Art of Scientific Computing (FORTRAN Version)", 1989, pp. v, 268-273, ISBN 0 521 38330, 7Press Syndicate of the University of Cambridge, Cambridge.

* cited by examiner

*Primary Examiner*—Hoon Song

(57) ABSTRACT

For scattered radiation correction in dual X-ray absorptiometry it is proposed to use the additional information supplied by the attenuation images in different energy ranges in a correction image area with homogeneous attenuation coefficients in order to determine the respective scattered radiation fraction. Toward that end, the inverse of the primary radiation function is considered and a search conducted for that scatter-to-primary ratio which leads to consistent mass per unit areas for the attenuation images recorded in different energy ranges.

18 Claims, 7 Drawing Sheets

METHOD FOR SCATTERED RADIATION CORRECTION

CROSS REFERENCE TO RELATED APPLICATIONS

This application claims priority of German application No. 10 2006 046 732.9 filed Sep. 29, 2006, which is incorporated by reference herein in its entirety.

FIELD OF THE INVENTION

The invention relates to a method for scattered radiation correction.

BACKGROUND OF THE INVENTION

A method of this kind is known from HINSHAW, D. A.; DOBBINS III, J. T.: Recent progress in noise reduction and scatter correction in dual-energy imaging, in: Proc. SPIE, 1995, Vol. 2432, pages 134-142. With said known method, scattered radiation correction is performed for each of the attenuation images recorded in different energy ranges by defining, for a given pixel, an empirically determined scattered radiation fraction as a function of the image value. The scattered radiation fraction determines the shape and width of a distribution function for the scattered radiation. The scatter contributions in adjacent pixels are calculated with the aid of the distribution function. The method is then repeated for further image values and the scatter contributions in the individual pixels are summed. Thus, a convolution of the image recorded by means of the detector device takes place with a distribution function, the width and shape of which depend on the image values of the attenuation image recorded by the detector device.

Scattered radiation correction is very important in dual X-ray absorptiometry.

More information about dual X-ray absorptiometry can be found in WARP, R. J.; DOBBINS, J. T.: Quantitative evaluation of noise reduction strategies in dual-energy imaging, in: Med. Phys. 30 (2), February 2003, pages 190-198.

In dual X-ray absorptiometry, the object to be examined, which is usually a patient, is irradiated by means of X-ray radiation in different energy ranges, whereby the dual X-ray absorptiometry can be effected by means of a single radiograph recording or a series of successively recorded radiographs. Typically, two radiographs are taken in succession.

In the first case, a dual detector having two different scintillation materials is used, the response characteristics of which have energy centers of mass lying as far apart from each other as possible. In the second case, succeeding images are recorded using as far as possible different X-ray spectra which, when X-ray tubes are used, can be generated by changes to the tube voltage by means of which the electrons are accelerated, or by selection of prefilters.

For each pixel of the recorded projection images it is possible to deduce the material composition in the beam path between the point X-ray source and the pixels from the attenuation characteristics in the different energy ranges. The projection images are also referred to in the following description as attenuation images. Furthermore, material composition is to be understood as meaning the mass per unit area of the different materials along the beam through the object to be examined.

In projection radiography using surface detectors, scattered radiation plays a significant role owing to the large solid angle recorded. In order to reduce the scattered radiation, anti-scatter grids are frequently used immediately above the detector input surface.

As a quantitative method, dual X-ray absorptiometry imposes higher requirements in terms of the accuracy of the measurement data than simple projection imaging as part of projection radiography. In spite of anti-scatter grids, the scattered radiation fraction falsifying the data may still be significant. For example, when images are recorded in the thoracic region, the air gap is usually very small, since the patient is positioned very close to the detector. As a result, in spite of anti-scatter grids, the intensity of the scattered radiation can still predominate over the primary intensity, especially in image regions with strong attenuation and at higher photon energies, corresponding to X-ray tube voltages in excess of 100 kV. Moreover, it is an empirical fact that the scattered radiation fractions are very different in the higher- and lower-energy image data. All in all, in spite of anti-scatter grids, the presence of scattered radiation in dual X-ray absorptiometry can lead to unreliable and in some cases unusable results, to negative material thicknesses for example.

For this reason computational scattered radiation correction methods are necessary in dual X-ray absorptiometry, in addition to the use of anti-scatter grids.

It should be noted at this point that the scattered radiation is also referred to in the following as secondary radiation. In contrast, the unscattered radiation recorded by the detector is referred to as primary radiation. The sum of primary radiation and secondary radiation, which yields the measured image values, is referred to as the total radiation.

A metrological method for determining the scattered radiation in accordance with the beam-stop technique is known from FLOYD, C. B.; BAKER, J. A.; LO, J. Y.; RAVIN, C. E.: Posterior Beam-Stop Method for Scatter Fraction Measurement in Digital Radiography, in: Investigative Radiology February 1992, Vol. 27, pages 119-123. This method is suitable for applications in the laboratory using phantoms, but hardly for clinical operation.

Various computational methods for scattered radiation correction within the framework of computed tomography are known from ZELLERHOFF, M.; SCHOLZ, B.; RÜHNSCHOPF, E.-P.; BRUNNER, T.: Low contrast 3D reconstruction from C-arm data, in: Proceedings of SPIE. Medical Imaging, 2005, Vol. 5745, pages 646-655. However, the known computational methods are usually fairly complex and time-consuming.

There is therefore a need for comparatively simple correction methods by means of which the image quality can be significantly improved.

SUMMARY OF THE INVENTION

Proceeding on the basis of this prior art, the object underlying the invention is therefore to specify a simple method for scattered radiation correction by means of which the image quality can be significantly improved.

This object is achieved by means of a method having the features of the independent claim. Advantageous embodiments and developments are set forth in claims dependent thereon.

With the method, the respective secondary radiation fraction of the attenuation images recorded in different energy ranges is determined from the image values of the attenuation images recorded in different energy ranges in a correction image area which maps an object region with a homogeneous absorption coefficient.

The inventive method comprises the following steps:

generating radiation by means of a radiation source and irradiating an examination object with the aid of said radiation;

directing the radiation at a detector device and recording attenuation images in different energy ranges by means of said detector device; and determining, by means of an evaluation unit connected downstream of the detector device, a secondary radiation fraction caused by scatter and correcting the attenuation images with regard to the secondary radiation fraction to a primary radiation fraction generated by attenuation.

With the method, the information available in addition as a result of the recording of attenuation images in different energy ranges is thus used to determine the scattered radiation fraction in an image area with a homogeneous attenuation coefficient. An object region with a homogeneous attenuation coefficient is understood in this context to mean an object region containing material with the same attenuation coefficient or containing materials whose attenuation coefficients essentially exhibit the same energy dependence and whose attenuation coefficients can be replaced approximately by multiplication of a density factor with the attenuation coefficient of a material. In the human or animal body, such material can be what is referred to as soft tissue. Since the secondary radiation fraction varies only slowly across an attenuation image, the scattered radiation correction obtained in this way can also be used to correct the secondary radiation fraction across the entire attenuation image.

In a preferred embodiment of the method, in order to determine the secondary radiation fraction of the attenuation images recorded in different energy ranges, a search is made for those secondary radiation fractions that are linked to primary radiation fractions, from which the same mass per unit area for the correction image area results in each case during the evaluation of the inverse primary radiation function. By means of this method use is made of the fact that the primary radiation functions are monotonous functions and can therefore be inverted and that the inversion of the primary radiation functions must necessarily yield matching mass per unit areas, since the correction area maps the same object region in each case.

In order to determine the secondary radiation fraction, use is preferably made of a predetermined relationship between primary radiation fraction and secondary radiation fraction as a function of the mass per unit area in the correction area. Since the ratio of secondary radiation fraction to primary radiation fraction usually depends on the mass per unit area, this dependence needs to be taken into account in the linking of secondary radiation fraction to primary radiation fraction. Since the relationship between secondary radiation fraction and primary radiation fraction as a function of the mass per unit area is based on general physical principles, this can be determined in advance and stored for example in tabular form.

A predetermined ratio of secondary radiation fraction to primary radiation fraction as a function of the mass per unit area in the correction area is preferably evaluated in order to determine the scattered radiation fraction. This ratio is known and validated for different materials.

In a further preferred embodiment, a predetermined relationship between the ratios of secondary radiation fraction to primary radiation fraction that are associated with the different energy ranges as a function of the mass per unit area is evaluated in order to determine the secondary radiation fraction. This enables the respective values for the secondary radiation fractions to be found by solving an implicit consistency equation. Finally the problem is thus reduced to a zero point determination which can be performed quickly and without great computational overhead.

It has been shown that the ratio of the ratios of secondary radiation fraction to primary radiation fraction that are associated with the different energy ranges is advantageously used for the relationship between the ratios of secondary radiation fraction to primary radiation fraction, since a constant value can be assumed by approximation for this ratio, thereby considerably simplifying the finding of the solution.

To that extent it is possible for a search to be made in the correction area in an attenuation image for a secondary radiation fraction and a secondary radiation fraction of another attenuation image linked thereto, these being linked to primary radiation fractions from which the same mass per unit area results in the correction area in each case during evaluation of the inverse primary radiation functions. The secondary radiation fraction is preferably calculated by equating the inverses of the primary attenuation functions dependent on the mass per unit area and replacing the primary radiation intensity by the measured image values of the attenuation images in the resulting consistency equation. Assuming, in a first approximation, a constant ratio that is independent of the mass per unit area, the implicit consistency equation containing the secondary radiation fraction as a variable can be solved. This method offers the advantage that the computational overhead is low.

The method steps can also be iterated in order to improve accuracy. On completion of the search for the secondary radiation fractions, the associated mass per unit area can be determined and the search for the scattered radiation fractions conducted again taking into account the previously determined mass per unit area. In a preferred embodiment, the consistency equation is solved iteratively by determining, on the basis of the calculated secondary radiation fraction, the mass per unit area from the inverse of the primary radiation function and determining a ratio, associated with the mass per unit area, of the ratios of secondary radiation fraction to primary radiation fraction associated with the different energy ranges. Accuracy in determining the secondary radiation fraction can be further improved by insertion in the consistency equation and repeated solving of the consistency equation.

The scattered radiation correction can be performed in each case at individual pixels of the attenuation image or determined in each case on the basis of image values averaged over a predetermined range. The secondary radiation fraction is preferably determined in each case in the area of interpolation points of a grid superimposed on the attenuation image and the secondary radiation fraction interpolated for pixels between the interpolation points.

In image areas that are associated with object regions with an inhomogeneous structure of the attenuation coefficient, the secondary radiation fraction that was calculated in an adjacent correction image area with a homogeneous attenuation coefficient is extrapolated into the image area with an inhomogeneous attenuation coefficient. This is possible because the scattered radiation caused by object regions with strong attenuation also makes itself noticeable in adjacent object regions with a homogeneous attenuation coefficient. It is therefore possible to extrapolate the secondary radiation fraction in the image area with an inhomogeneous attenuation coefficient from the characteristic of the secondary radiation fraction determined in the vicinity of the image area with an inhomogeneous attenuation coefficient. An object region with an inhomogeneous attenuation coefficient is to be understood in this context as an object region containing different materials that have attenuation coefficients with different energy dependence, with the result that the attenuation coefficients cannot be replaced approximately by multiplication of a density factor by the attenuation coefficient of a material. In the human or animal body, for example, object regions which include bone tissue and soft tissue are object regions with an inhomogeneous attenuation coefficient.

BRIEF DESCRIPTION OF THE DRAWINGS

Further characteristics and advantages of the invention will emerge from the following description in which exemplary embodiments of the invention are explained in detail with reference to the accompanying drawing, in which.

DETAILED DESCRIPTION OF THE INVENTION

Figure 1:
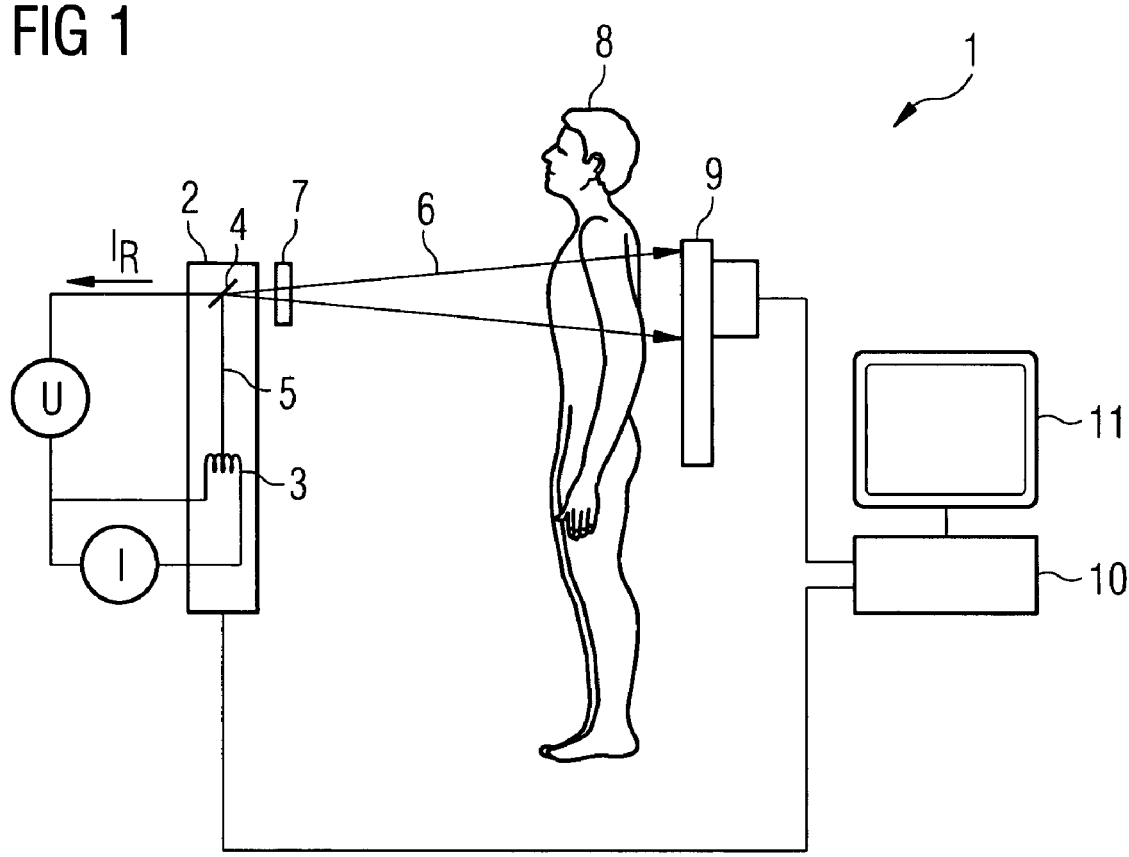
FIG. 1 shows a device for dual X-ray absorptiometry.

FIG. 1 shows an X-ray system 1 by means of which radiographs can be taken for dual X-ray absorptiometry. The X-ray system 1 comprises an X-ray tube 2 which has a cathode 3 formed by a filament. The filament 3 can be heated with the aid of a heating current I. In this arrangement electrons are emitted by the cathode 3 and accelerated with the aid of a tube voltage U in the direction of an anode 4. This results in an electron beam 5 which strikes the anode 4 in a focal spot. The electrons decelerated in the anode 4 generate X-ray radiation 6 which initially passes through a prefilter 7 so as to suppress the low-energy component, said prefilter 7 having the effect of a spectral filter. The prefilters 7 are typically thin copper plates which can be introduced in different thicknesses into the beam path of the X-ray radiation 6. The X-ray radiation 6 then penetrates a patient 8 to be examined.

The X-ray radiation 6 that has passed through the patient 8 is captured by an X-ray detector 9 which records an attenuation image of the patient 8. At the same time the structure of the material in the patient 8 that is attenuating the X-ray radiation 6 is projected onto the X-ray detector 9. Radiographs containing the attenuation images are therefore also referred to as projection images.

The X-ray detector 9 is preferably a semiconductor-based flat-panel detector or surface detector which has a plurality of detector elements by means of which a digital X-ray image can be generated. The detector elements each record a picture element. The individual picture elements are also referred to as pixels.

Connected downstream of the X-ray detector 9 is an evaluation unit 10 which usually forms a linear combination of the attenuation images recorded by variation of the tube voltage U and the prefilters 7 in different energy ranges of the X-ray radiation 6. The combination image generated by the linear combination of the attenuation images recorded in different energy ranges is displayed on a display unit 11.

The linear combination of the attenuation images can be, for example, the formation of a difference by means of which the bone structure of the patient 8 is eliminated from the combination image. The combination image generated in this way contains the attenuation structure of the soft tissue, which is of advantage in particular for examinations of the lung.

In order to take attenuation images in different energy ranges, the tube voltage U and the prefilters 7 in particular are varied. For example, a lower tube voltage U can be used for the attenuation image in the low-energy range. In addition, the prefilters 7 can have a low material strength, such that the low-energy part of the spectrum generated by the X-ray tube 2 is suppressed only slightly. Conversely, a high tube voltage U can be used for the attenuation images in the high-energy range. Furthermore, prefilters 7 having greater material strength can be used which only allow the high-energy part of the X-ray spectrum generated by the X-ray tube 2 to pass through.

Because scattered radiation correction plays a significant role with regard to the usability of the combination images, a correction method by means of which the scattered radiation effects can be reduced is described below. Said correction method is essentially based on the following consistency condition: As the attenuation images recorded in different energy ranges represent the same object, identical material thicknesses must result for the object to be examined from the attenuation images. If this is not the case and further systematic errors can be ruled out, the deviations must in each case be due to the scattered radiation fraction. In an area with a homogeneous attenuation structure, the measured projection values can therefore be used to calculate back to the respective scattered radiation fractions.

The correction method for estimating the scattered radiation fraction will now be described in detail.

1. Punctual Estimation of the Scattered Radiation Using Consistency Condition:

The signal formation of the X-ray radiation 6 which penetrates the patient 8 is essentially determined by the emission spectrum $Q_U(E)$, i.e. the energy spectrum of the photons emitted as bremsstrahlung ("braking radiation") at the anode and dependent on the applied tube voltage U, as well as by the transparency $T_F(E)$ of the spectral filters used and the spectral response sensitivity $\eta_D(E)$ of the X-ray detector 9.

The resulting effective normalized spectral distributions W(E;U) are defined by:

$$W(E;U) = Q_U(E) T_F(E) \eta_D(E)/c_U \qquad (\#1a);$$

where the factor $c_U$ normalizes the integrated effective nominated spectral distribution to the value=1.

Figure 2:
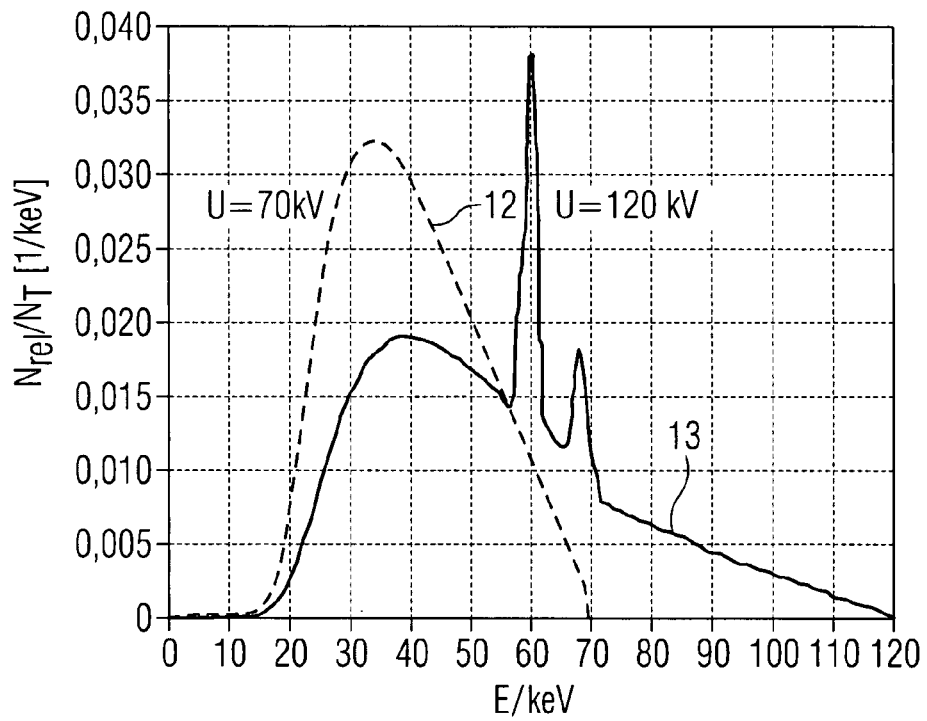
FIG. 2 shows two photon spectra of an X-ray tube with an anode made of tungsten recorded at different tube voltages.

Examples of two effective spectral distributions corresponding to the tube voltages 60 kV and 120 kV are shown in FIG. 2. FIG. 2 is a graph in which the relative photon frequency $N_{rel}/N_T$ per 1-keV interval is plotted against the photon energy E in keV, where $N_T$ is the total number of photons. In this case an X-ray spectrum 12 is assigned to a tube voltage of 70 kV and an X-ray spectrum 13 to a tube voltage of 120 kV.

Figure 3:
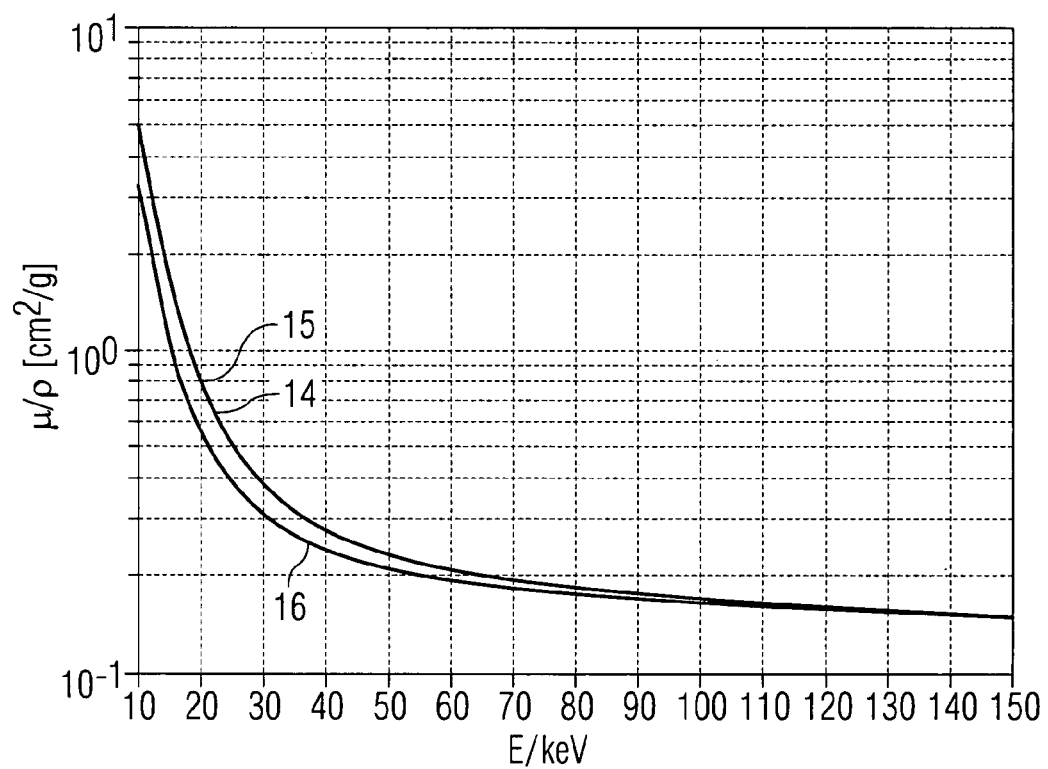
FIG. 3 shows the shape of the mass attenuation coefficient as a function of the photon energy for different parts of the body.

The dependence of the mass attenuation coefficient for water $(\mu/\rho)(E)$ on the photon energy E is shown in FIG. 3. A mass attenuation curve 14 for water is in this case roughly congruent with a mass attenuation curve 15 for blood. Fatty tissue, in contrast, has a mass attenuation curve 16 deviating from the two other mass attenuation curves 14 and 15. Except for a scaling factor, the mass attenuation curve 16 does, however, have a similar energy dependence. It can therefore be assumed that blood and fatty tissue have the same attenuation characteristics as water and differ only with regard to the density of water, which is equivalent to 1 g/cm³.

Below we consider two measurement values for the same object, recorded using two different tube voltages $U^1$ and $U_2$, possibly also different tube-side or detector-side filters. We designate the effective spectral distributions by:

$$W_1(E) = W(E;U_1),\ W_2(E) = W(E;U_2) \qquad (\#1b,c).$$

It is assumed that all the usual calibration corrections for digital X-ray detectors 9 have been carried out. Specifically, these are a dark image subtraction and a correction of the different sensitivities of the pixels. It is also assumed that a correct $I_0$ normalization has been performed. In this context an $I_0$ normalization is understood to mean the following: The full unattenuated intensity $I_0$ without attenuating object is determined for both spectra and each intensity measurement value at each pixel of the X-ray detector 9 is normalized by means of division by the corresponding $I_0$ value. The following statements always relate to normalized intensity values, be they primary radiation, scattered radiation or measured total radiation intensity values which consist of the sum of primary radiation and scattered radiation.

The following designations are also used in the statements below:

$J_1$, $J_2$ Normalized measured total intensities in the spectrum $W_1(E)$ or $W_2(E)$, $P_1$, $P_2$ Normalized, initially unknown primary intensities, $S_1$, $S_2$ Normalized, initially unknown scattered radiation intensities.

Theoretically, the following holds for the normalized primary intensities (=primary attenuations) in the spectra $W_1(E)$ and $W_2(E)$ in the case of soft tissue if the respective X-ray measurement beam passes through the same effective path length X [cm] or mass per unit area X [g/cm²]:

$$P_1 = F_1(X) = \int_0^{eU_1} e^{-\mu(E)X} W_1(E) dE, \qquad (\#2)$$

$$P_2 = F_2(X) = \int_0^{eU_2} e^{-\mu(E)X} W_1(E) dE. \qquad (\#3)$$

It should be pointed out that in equations (#2, #3), $\mu$ in the exponent is to be understood as the mass attenuation coefficient if X is interpreted as the mass per unit area. If, on the other hand, X is interpreted as the distance, then $\mu$ is to be understood as the linear attenuation coefficient.

The effective spectra $W_1(E)$ and $W_2(E)$ can be regarded as known. Consequently, the primary radiation functions $F_1(X)$, $F_2(X)$ describing the primary attenuation can be precalculated in principle as functions of the material thickness X or else determined experimentally. As they decrease strictly monotonously with X and are therefore unambiguous, the inverse primary radiation functions exist. Accordingly, it can be assumed that the inverse primary radiation functions of $F_1(X)$, $F_2(X)$ are in principle available in precalculated and tabulated form. These inverse primary radiation functions shall be designated by $G_1(P)$, $G_2(P)$:

$$G_1 = F_1^{-1} \qquad (\#4),$$

$$G_2 = F_2^{-1} \qquad (\#5).$$

The equations (#2) to (#5) describe the physics of the radiation attenuation with different spectra for one and the same mass per unit area X If the photons travel the same distance through the patient 8 in each case, the following consistency condition must therefore apply:

$$G_1(P_1) = G_2(P_2) = X \qquad (\#6).$$

Ignoring noise and assuming that no other measurement errors occur, the measured total radiation intensity is equal to the sum of primary and scattered radiation intensity:

$$P_1 + S_1 = J_1 \qquad (\#7),$$

$$P_2 + S_2 = J_2 \qquad (\#8).$$

The three equations (#6) to (#8) do not yet unambiguously determine the four unknowns $P_1$, $P_2$, $S_1$, $S_2$.

Since the $P_k$ are specified as soon as the $S_k$ have been determined and vice versa, the problem can be reduced to two unknowns. Toward that end we introduce the relative scatter fractions $$q_1 = S_1/J_1,\ q_2 = S_2/J_2 \qquad (\#9),\ (\#10),$$

and the relative primary fractions $$r_1 = 1 - q_1 = 1 S_1/J_1 \qquad (\#11),$$

$$r_2 = 1 - q_2 = 1 - S_2/J_2 \qquad (\#12).$$

In this way the equations (#6)-(#8) are reduced to a single consistency equation:

$$G_1(r_1 J_1) = G_2(r_2 J_2) \qquad (\#13).$$

With this one equation for the two unknowns $r_1$, $r_2$, the normalized scattered radiation intensities $S_1$, $S_2$ sought for the scattered radiation correction are correlated by $$S_1 = q_1 J_1 = (1 - r_1) J_1 \qquad (\#14a),$$

$$S_2 = q_2 J_2 = (1 - r_2) J_2 \qquad (\#14b).$$

In order to be able to obtain an unambiguous solution for the two unknowns $r_1$, $r_2$, a second independent equation is required.

A second independent equation is produced as a result of using an empirical relationship which can be established between the relative scatter fractions as a function of the material thickness in different spectra.

Figure 4:
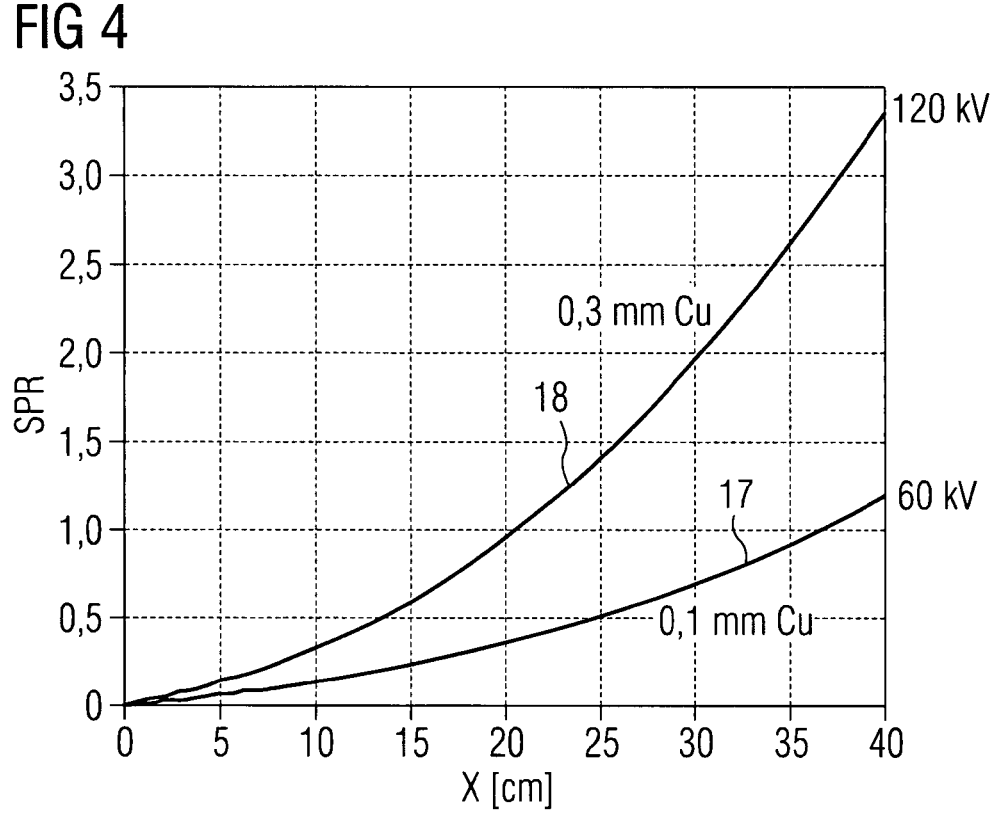
FIG. 4 shows a diagram in which the scatter-to-primary ratio is entered as a function of the water thickness for different tube voltages.

This relationship can be determined by means of Monte Carlo calculations. For example, the diagrams in FIG. 4 in which what is termed the scatter-to-primary-ratio (SPR) is represented as a function of the water thickness X are produced for two X-ray spectra at 60 kV and 120 kV tube voltage using a commercial anti-scatter grid. FIG. 4 shows in each case the ratios $$s_1 = S_1/P_1, \quad s_2 = S_2/P_2 \qquad (\#15a), (\#15b).$$

An SPR curve 17 gives the ratio $s_1$ corresponding to a tube voltage U=60 kV and a prefilter 7 with 0.1 mm copper, and an SPR curve 18 illustrates $s_2$ corresponding to a tube voltage U=120 kV and a prefilter 7 with 0.3 mm copper.

Figure 5:
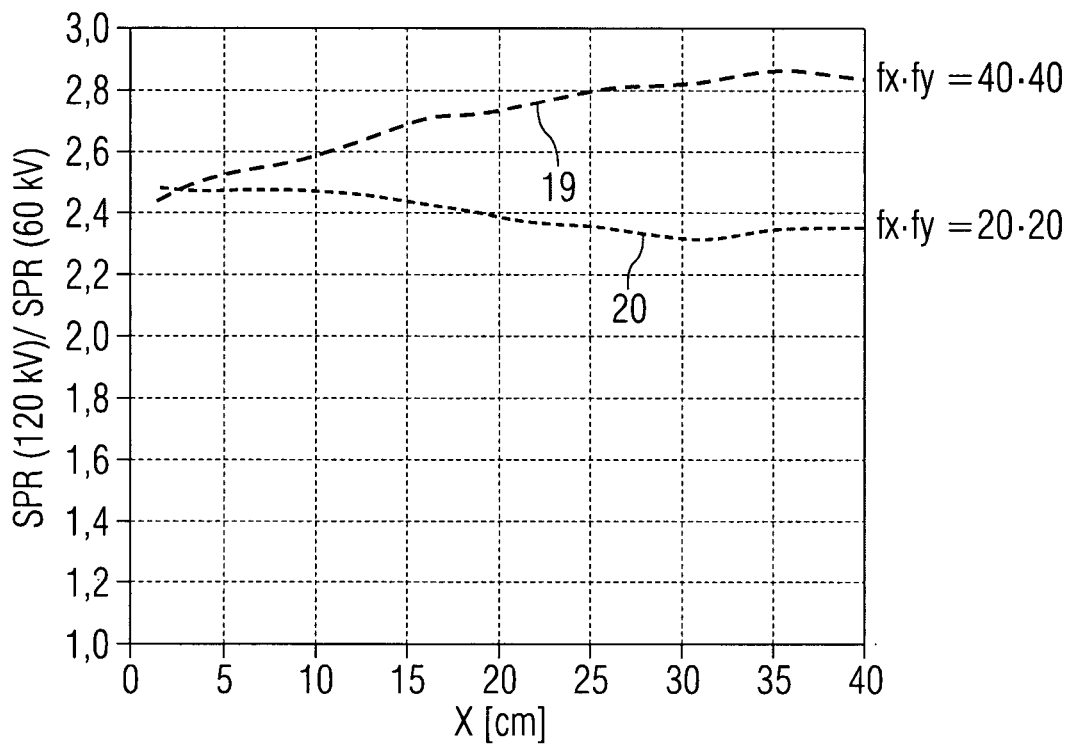
FIG. 5 shows a diagram which plots the curve of the ratio of the scatter-to-primary ratios associated with different tube voltages as a function of the water thickness.

FIG. 5 shows the ratio $$c(X) = s_2(X)/s_1(X) \qquad (\#16)$$

as a function of the water thickness X. In FIG. 5, a ratio curve 19 shows the shape of the ratio c(X) for a detector field size of 40×40 cm², and a ratio curve 20 shows the shape of c(X) for a detector field size 20×20 cm². An air gap of 2 cm and an anti-scatter grid of type 15/80 were used in each case. A prefilter 7 with 0.1 mm copper was used for the recording at U=60 kV, and a prefilter 7 with 0.3 mm for the recording at U=120 kV. Interestingly it is shown that this ratio c(X) is only very weakly dependent on X and in wide ranges of X can be assumed as constant in a first approximation.

Before we can insert in equation (#13), we still need the conversion from $s_1$, $s_2$ into $r_1$, $r_2$, i.e. the conversion of the SPR into relative primary fractions.

Generally the following applies to the conversion, where the indices 1, 2 can be omitted:

$$r = r(s) = \frac{1}{1+s}. \qquad (\#17)$$

If this is inserted together with equation (#16) with suitable constant SPR ratio c, into equation (#13), then we obtain the unambiguously solvable condition equation for $s_1$ $$H(s_1) = G_1(r(s_1)J_1) - G_2(r(cs_1)J_2) = 0 \qquad (\#18)$$

$s_1$ is the SPR for the measurement value $J_1$ with the low-energy spectrum.

The solution $s_1$ of equation (#18) can be calculated using a standard method for zero point determination in nonlinear equations, for example using the Newton method or bisection search method. Methods of this kind are described for example in PRESS, FLANNERY, TEUKOLSKY, VETTERLING: Numerical Recipes. The Art of Scientific Programming, Cambridge University Press, S. 1992, Chapter 9, p. 353, p. 362.

Successive insertion into the equations (#17) and (#16) as well as (#14a, b) then yields the searched-for normalized scattered radiation intensities $$S_1 = \frac{s_1}{1+s_1} J_1 \qquad (\#19a, b)$$
$$S_2 = \frac{cs_1}{1+cs_1} J_2.$$

2. Iterative Improvement:

Using equation (#6) and (#7) we obtain from $$G_1(J_1 - S_1) = X \qquad (\#20)$$

the associated material per unit area X. In this way we can obtain a better value for c=c(X) from the relation (#16) and again insert in equation (#18). These method steps can be iterated if necessary.

3. Prerequisites:

A number of prerequisites must be fulfilled for the method described here to be executable in practice.

To ensure that the use of the consistency condition leads to usable results for scattered radiation correction, the measurements must satisfy high accuracy requirements. Otherwise significant errors are likely in the estimation of the scattered radiation fractions.

On the one hand the functional relationship between radiological attenuation and material thickness, by default water, must be known theoretically as accurately as possible and validated experimentally.

On the other hand the measurements with the X-ray detector 9 must be as accurate as possible. This requires above all a careful calibration of the detector system: In particular, no systematic deviations must occur between the two energies. Moreover, precise $I_0$ determination for both energies is very important, i.e. correct determination of the unattenuated intensity values without radiation-attenuating object. At the same time a correction of the detector characteristic curve must also be performed for the case of overradiation, i.e. for the situation in which the detector signal passes into saturation at high radiation intensity.

The correction method described here also assumes knowledge of the scatter-to-primary ratio between the higher- and low-energy measurement, as indicated in equation (#16) and (#18). This ratio can be determined in advance by means of measurements or Monte Carlo calculations and from experience is only weakly dependent on the material thickness, but substantially dependent on the anti-scatter grid and the air gap between X-ray detector 9 and patient 8. Consequently, knowledge of the width of the air gap is important for its application and must be taken into account if the patient 8 is not in immediate proximity to the X-ray detector 9.

In addition, radiologically equivalent material is assumed initially. To that extent the energy dependence of the mass attenuation coefficients $(\mu/\rho)(E)$ in the considered spectral range should be practically identical, but the density of the material can vary. This applies for example to soft tissue such as muscles, organ tissue, brain mass, and blood, as well as to hydrocarbon-based plastics, but not to bone or contrast agents. Taking tissue or substances of this kind into account requires separate measures.

The spatial distribution of the scattered radiation was initially ignored. To that extent an individual pixel is considered punctually on the X-ray detector 9 and the assumption made that said pixel is representative of a largely homogeneous environment with the extension of some medium scatter distances, i.e. with an extension of several cm. This punctual consideration can also be regarded as a global estimation of a scattered radiation background for an average value in a region of interest (ROI). In any case use is made here of the fact that the spatial distribution of the scattered radiation is very low-frequency and in a first approximation can be replaced by a suitable constant value.

4. Extension of the Scattered Radiation Correction Over the Entire Image

Barring noise, the spatial distribution of the scattered radiation is very smooth and therefore low-frequency. This means that it suffices to determine the scattered radiation at very few points on the detector surface either punctually or in regions of interest. The simplest approximation is therefore a matching constant average value for the secondary radiation intensity.

For a global estimation of the average scattered radiation background intensity it suffices to select a suitable region of interest in the soft tissue area and in each case to form an average value over this region of interest for the low—and the higher-energy projection image. For this value pair $\overline{J}_1$, $\overline{J}_2$, the corresponding value pair $\overline{S}_1$, $\overline{S}_2$ of the scattered radiation intensities is then determined in accordance with the above-described method. The overbars are intended to express that these values are estimated, averaged or even constant values.

The scattered radiation correction then consists in the subtraction of the estimated scattered radiation intensities from the respective uncorrected normalized intensity distributions:

$$\tilde{P}_1(x,y) = J_1(x,y) - \overline{S}_1,$$

$$\tilde{P}_2(x,y) = J_2(x,y) - \overline{S}_2 \quad (\#21)$$

On the left-hand side are the corrected primary distributions. (x, y) designate pixel coordinates on the detector. The tilde is intended to indicate that the data is corrected data, i.e. estimations based on a correction.

Since a constant value is only a very rough approximation, it can happen that negative values occur in equation (#21) during the subtraction. Physically nonsensical values of this kind must be prevented in any event. One measure is the choice of a suitable region of interest in the area of strong attenuation for the purpose of globally determining the scattered radiation. An area with strong attenuation is an area with small $J_{1,2}$ values.

Another measure is, instead of the subtractive correction in equation (#21), to perform a multiplicative scattered radiation correction:

$$\tilde{P}_1(x, y) = J_1(x, y) \frac{1}{1 + \frac{\overline{S}_1}{J_1(x, y)}} \quad (\#22)$$

$$\tilde{P}_2(x, y) = J_2(x, y) \frac{1}{1 + \frac{\overline{S}_2}{J_2(x, y)}}.$$

For the case $\overline{S}_1 \ll J_1(x,y)$ and $\overline{S}_2 \ll J_2(x,y)$, (#22) transitions into (#21).

The location dependence of the scattered radiation background can also be recorded by applying the correction method described above in connection with an individual pixel on a uniform coarse grid of regions of interest or sampling points on the detector and expanding the result by means of interpolation from the coarse grid onto the original fine pixel grid. The corrections according to equations (#21) and (#22) must then be expanded analogously: $\overline{S}_1$, $\overline{S}_2$ are then no longer constants, but functions dependent on the pixel coordinates (x, y), even if this dependence is usually only weak.

It should be noted that the interpolation can also be carried out onto the original fine grid by convolution of the values determined on the coarse grid for the scattered radiation fractions by means of a broad distribution function.

Conventional correction methods also take into account the fact that the scattered radiation is spatially very low-frequency by means of smoothing convolution operations. Corresponding methods are described in ZELLERHOFF, M.; SCHOLZ, B.; RÜHRNSCHOPF, E.-P.; BRUNNER, T.: Low contrast 3D reconstruction from C-arm data. In: Proceedings of SPIE. Medical Imaging, 2005, Vol. 5745, pp. 646-655. The combination of the approach described here with more complex convolution models of said type is possible in principle. For example, the scattered radiation fractions can be determined by means of one of the methods described here and, in parallel therewith, by means of a conventional method and the results subsequently averaged.

5. Validation of the Correction Method

Monte Carlo simulation calculations were performed in order to validate the method.

The simulation calculations were performed for the following case:

The X-ray radiation is generated by an X-ray tube with tungsten anode which generates X-ray spectra according to FIG. 2 at tube voltages of 60 kV and 120 kV. A prefilter 7 with 0.1 mm copper was used at the tube voltage of U=60 kV and a prefilter 7 with 0.3 mm copper at the tube voltage of U=120 kV.

The gap between X-ray source and flat-panel detector is 180 cm and the collimated field size on the detector 40×40 cm². A focused anti-scatter grid of type 15/80 is also used. An anti-scatter grid of said kind has an aspect ratio of 15 and 80 line pairs/cm.

An elliptical cylinder of water was selected as the object to be examined or scatter object. The longitudinal axis of the cylinder was aligned parallel to the detector plane. The transversal elliptical axis which ran in the direction of the X-ray beams, i.e. at right angles to the detector surface, was 20 cm long and the lateral elliptical axis which ran parallel to the detector surface was 50 cm long. The cylinder therefore projected laterally beyond the detector. The air gap, which is equal to the smallest distance between object and detector, was 2 cm.

The results of the simulation are shown in FIGS. 6 to 11.

The Monte Carlo calculations yield the primary and scattered radiation intensity distributions over the detector cross-section and the unattenuated intensity values that are required for $I_0$ correction and normalization.

Figure 6:
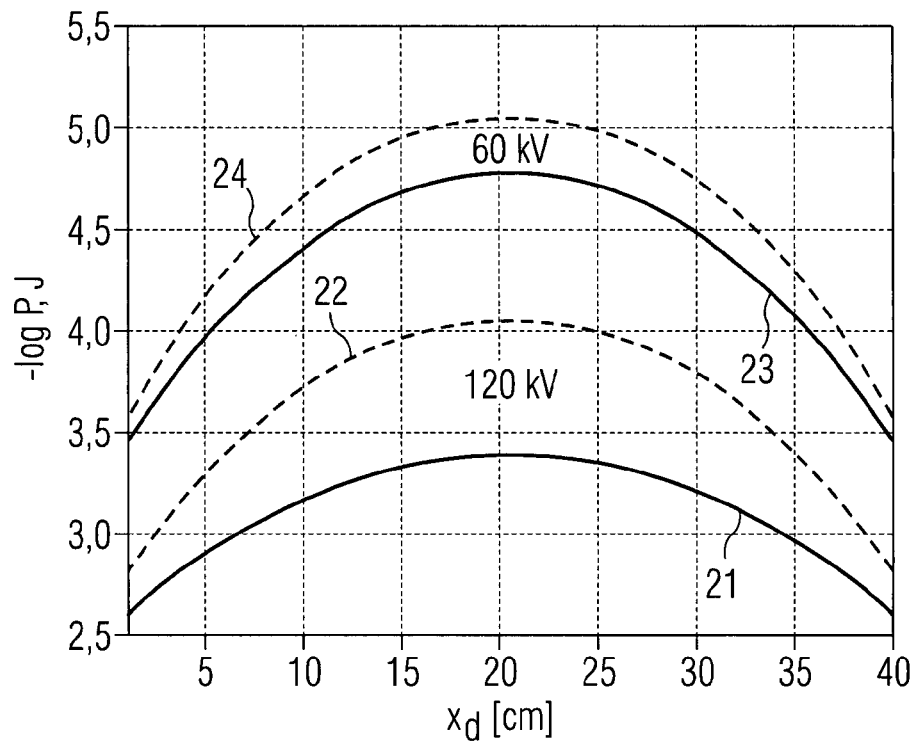
FIG. 6 shows a diagram which plots the uncorrected and corrected logarithmized projection values which result from a Monte Carlo simulation performed on a water cylinder.

FIG. 6 shows the logarithmized projection profiles of the primary radiation $P_1$, $P_2$ and the logarithmized projection profiles of the total radiation $J_1$, $J_2$ for both spectra. The projection profiles are in each case plotted along a detector row with detector coordinates $x_d$. The total radiation is equal to the sum of primary radiation and scattered radiation and corresponds to the uncorrected image values. The negative logarithm both of the total radiation and of the primary radiation is shown, since the normalized attenuation values are always less than 1. A projection profile 21 represented by an unbroken line reproduces the uncorrected total radiation $J_2$ for U=120 kV. A further projection profile 22 represented by a dashed line in FIG. 6 illustrates the corrected total radiation for U=120 kV, this being equal to the primary radiation $P_2$. Correspondingly, a projection profile 23 represented by an unbroken line indicates the curve of the uncorrected total radiation $J_1$ at U=60 kV. Similarly for U=60 kV, a projection profile 24 indicates the curve of the total radiation corrected to the primary radiation $P_1$.

Figure 7:
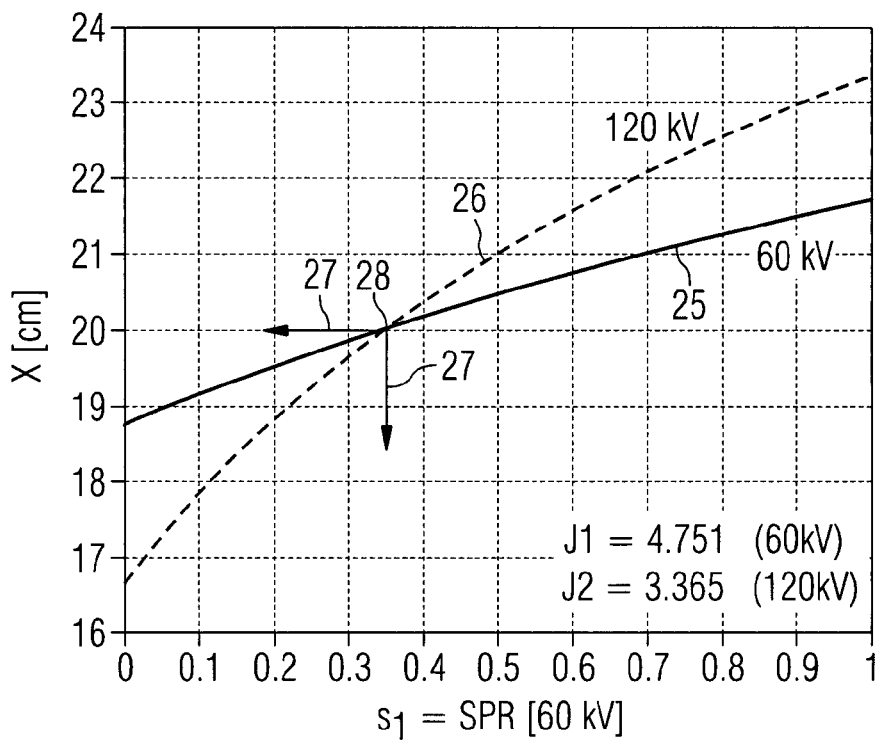
FIG. 7 shows a diagram serving to illustrate the solution of a consistency method for determining the scatter fraction.

FIG. 7 illustrates the solution of the consistency equation (#13) for the maximum logarithmized projection values in the center of the water cylinder. FIG. 7 shows the inverse primary radiation functions $G_1$ and $G_2$ as a function of $s_1$. To that extent the water thickness X is plotted against $s_1$ in each case. A curve 25 represented by an unbroken line in FIG. 7 illustrates the shape of the inverse primary radiation function $G_1$ and a further curve 26 represented by a dashed line in FIG. 7 shows the shape of the inverse primary radiation function $G_2$. What is being sought here is the SPR value $s_1$ in equation (#15a) for which the consistency equation is satisfied. The arrows 27 show the point of intersection 28 of the curves 25 and 26 for 60 and 120 kV. The equivalent water thickness X comes out at exactly 20 cm and $s_1 \approx 0.35$, which also accords with FIG. 4. It should be emphatically pointed out that this result was produced without the use of a table according to FIG. 4. All that was used was the ratio c=2.7 according to FIG. 5.

Figure 8:
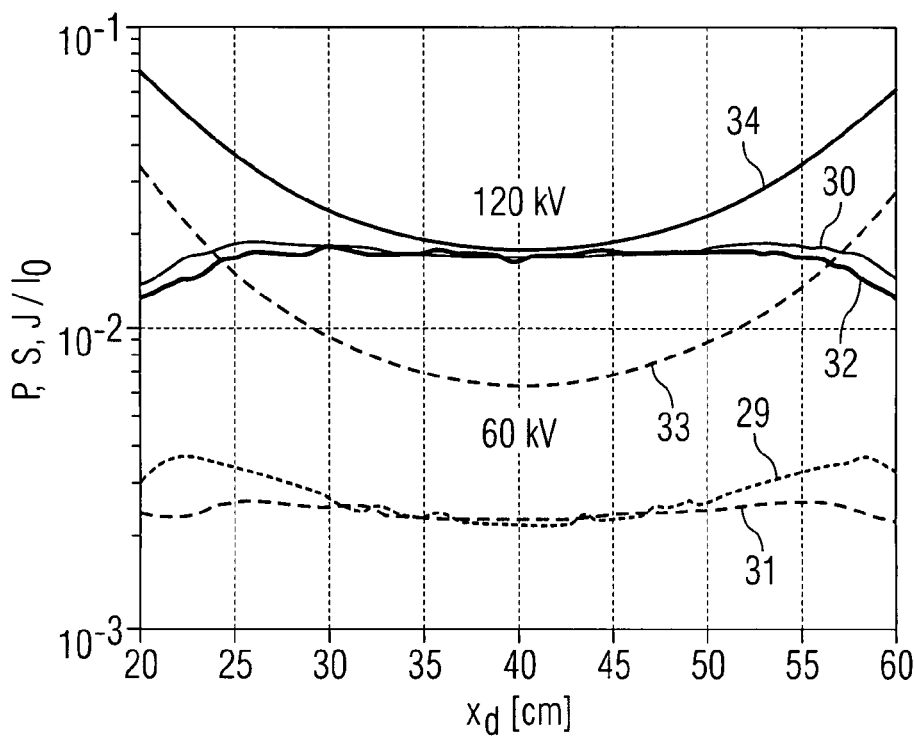
FIG. 8 shows a diagram which plots the normalized intensity values which result from the consistency method in comparison with the exact normalized intensity values along a detector row.

FIG. 8 shows the normalized scattered radiation distributions over a width of 40 cm in the central detector row: Curves 29 and 30 show the exact scatter distributions according to Monte Carlo simulation. The curves 31 and 32 show the results of the estimation according to equation (#19a and b). Based on FIG. 8, it emerges that the scattered radiation is somewhat underestimated at the edge of the detector and the water cylinder. The primary distributions determined by Monte Carlo simulation are represented in FIG. 8 by curves 33 and 34.

Figure 9:
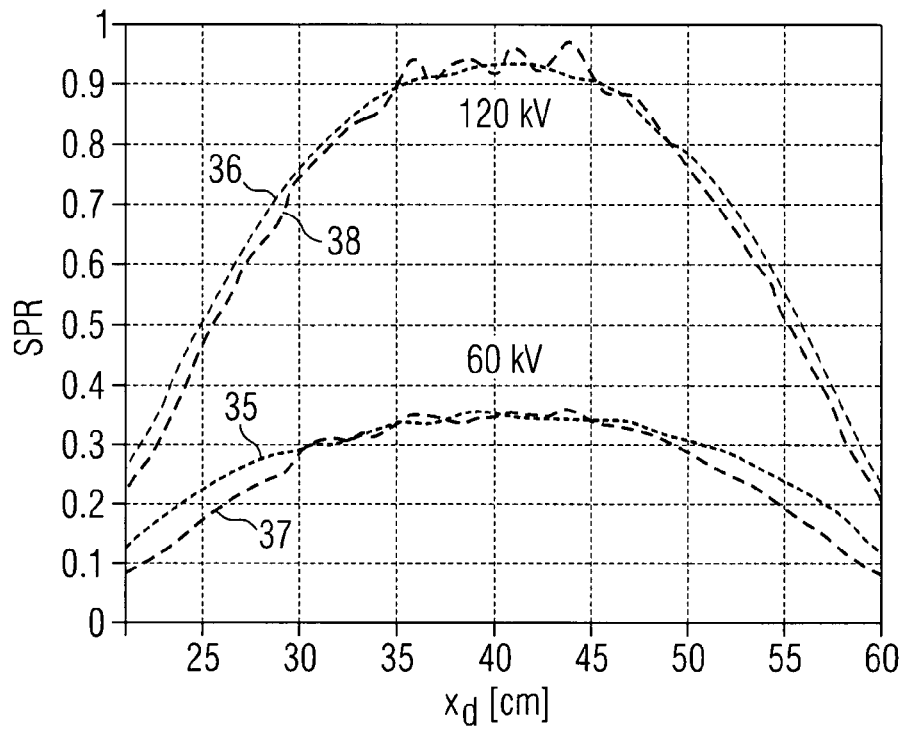
FIG. 9 shows a diagram in which the scatter-to-primary ratio which results from the consistency method is depicted in comparison with the exact scatter-to-primary ratio along a detector row.

FIG. 9 shows the distribution of the scatter-to-primary ratio over a width of the central detector row. The SPR determined by Monte Carlo simulation is in each case represented by curves 35 and 36, while the SPR determined by means of the consistency method is illustrated by curves 37 and 38. The underestimation at the edge is now no longer so pronounced.

Figure 10:
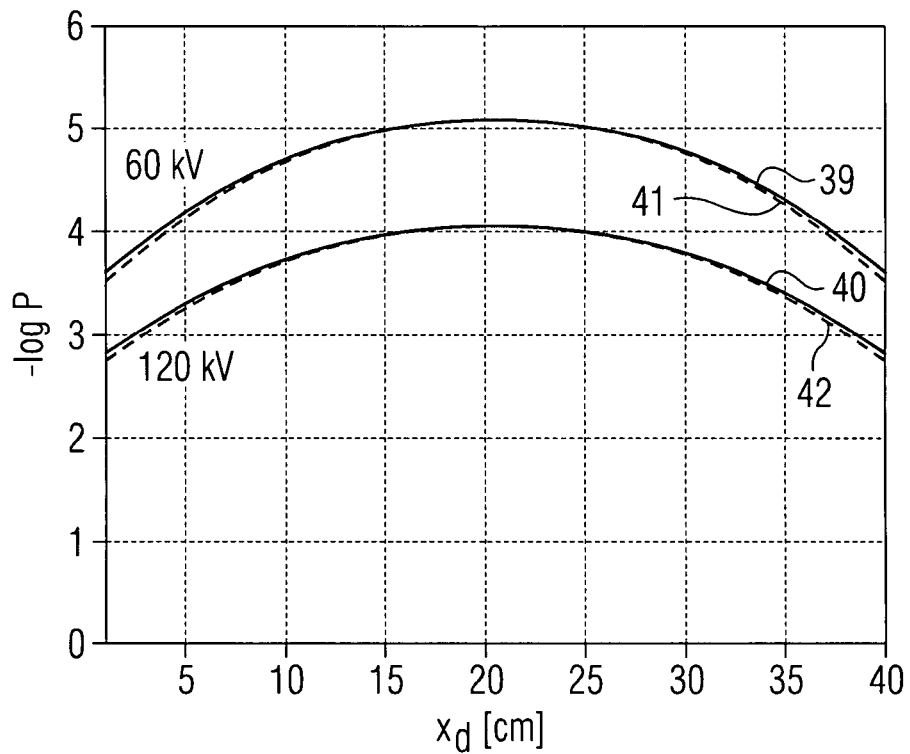
FIG. 10 shows a diagram which plots the logarithmized projection values which result from the consistency method in comparison with the logarithmized projection values for different tube voltages along a detector row.

Referring to FIG. 10, it can be seen how little the logarithmized projection profiles 39 and 40 determined with the aid of the Monte Carlo simulation (represented by unbroken lines) and the scatter-corrected logarithmized projection profiles 41 and 42 (represented by dashed lines) actually deviate from one another.

Figure 11:
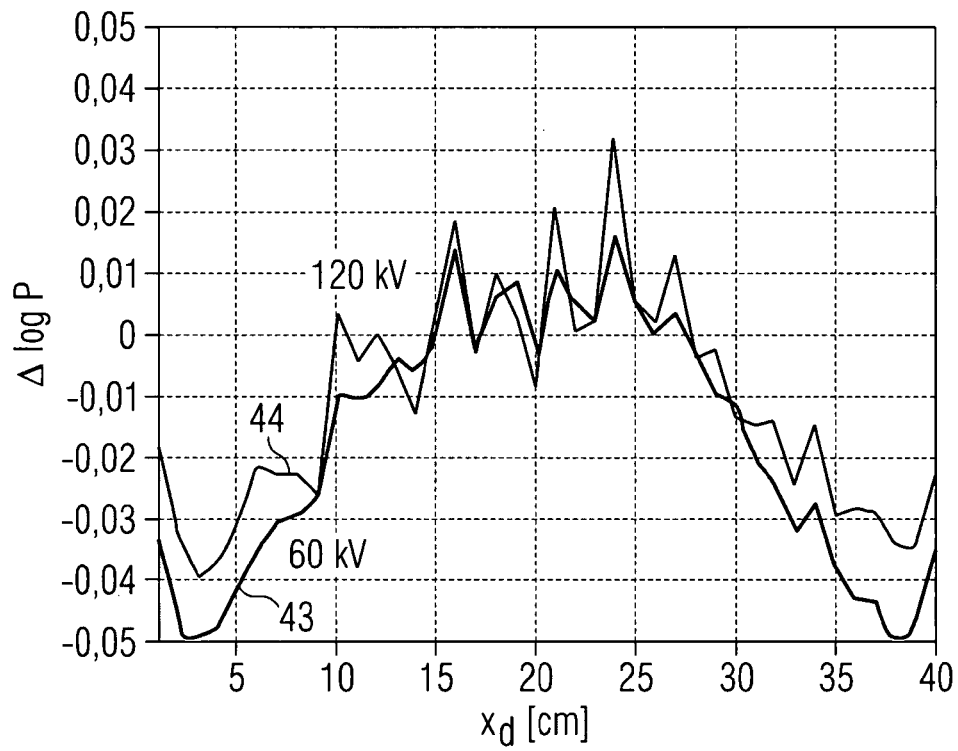
FIG. 11 shows a diagram in which the error in the determination of the logarithmized projection values for different tube voltages along a detector row is depicted.

In the diagram according to FIG. 11, finally, error curves 43 and 44 are shown. The error curves in FIG. 11 exhibit maximum errors of the logarithmized projection values of 0.04-0.05 at the detector edge. With effective attenuation coefficients of 0.2-0.25/cm, this corresponds to an inaccuracy of only approximately 2 mm path length in water.

6. Taking Bone into Account

Figure 12:
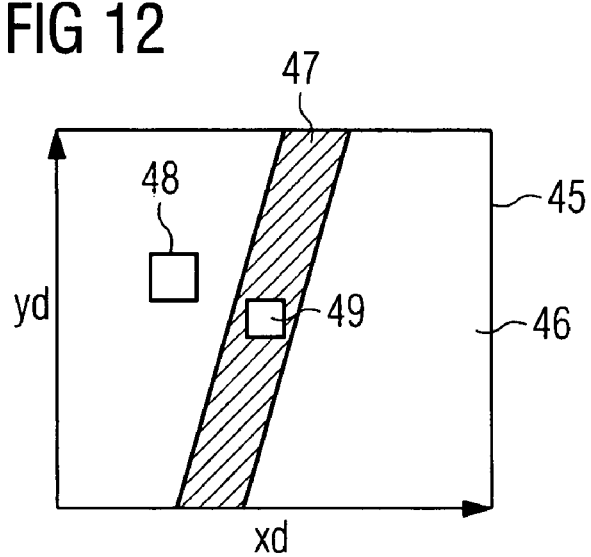
FIG. 12 shows an attenuation image with an inhomogeneous image area and a homogeneous image area.

In the statements made thus far the presence of radiologically similar material was assumed, in particular water-like soft tissue. This assumption was incorporated in the important equations (#2), (#3), (#16), (#18), (#19b). FIG. 12, for example, shows an attenuation image 45 with a homogeneous image area 46 and an inhomogeneous image area 47. In the homogeneous image area 46, only soft tissue is imaged, whereas in the inhomogeneous image area 47 both soft tissue and bone are imaged. Within the scope of the previous statements made the scattered radiation correction was described in a correction area 48 which is located in the homogeneous image area 46. The scattered radiation correction in a correction area 49 can be now carried out as follows:

A first simple possibility of taking bone tissue into account is the following: The selection of suitable regions of interest for estimating the scattered radiation is restricted to regions in which essentially only soft tissue occurs in the beam path. The extrapolation into the bone region can then be performed as follows, for example: A two-dimensional interpolation or extrapolation of the estimated scattered radiation intensity can be performed for example from the surrounding pixels assigned to the soft tissue region into the bone region. However, this can lead to an overestimation of the scattered radiation intensity in the bone region in which, typically, a stronger radiation attenuation takes place. The overestimation of the scattered radiation fraction can possibly be counteracted by computing a table containing correction factors in advance with the aid of Monte Carlo simulation. The relative reduction in the relative scatter fractions defined in the equations (#9, 10) as a function of the bone fraction along the measurement beam can be read out from the table. The scattered radiation intensities $S_1$ and $S_2$ estimated previously by interpolation or extrapolation should then be corrected by means of these correction factors.

A further possibility is, for example, is to estimate the local SPR in the surrounding pixels assigned to the soft tissue region as part of the scattered radiation estimation. The estimation is produced for example as the solution of the equation (#18) from which $s_1$ and hence $s_2 = cs_1$ can be determined. These SPR values can now extrapolated or interpolated into the bone region and the scattered radiation intensities within the bone region can be determined by means of equation (#19a and b).

7. Method Sequence

The scatter correction methods described here are in each case scatter pre-reconstructive methods which determine the scattered radiation fraction on the basis of the attenuation images, without reference to at least approximately determined three-dimensional volume images of the object that is to be examined. Rather, with said methods, the additional information that is available as a result of the attenuation images recorded in different energy ranges is used to estimate the scattered radiation fraction.

Figure 13:
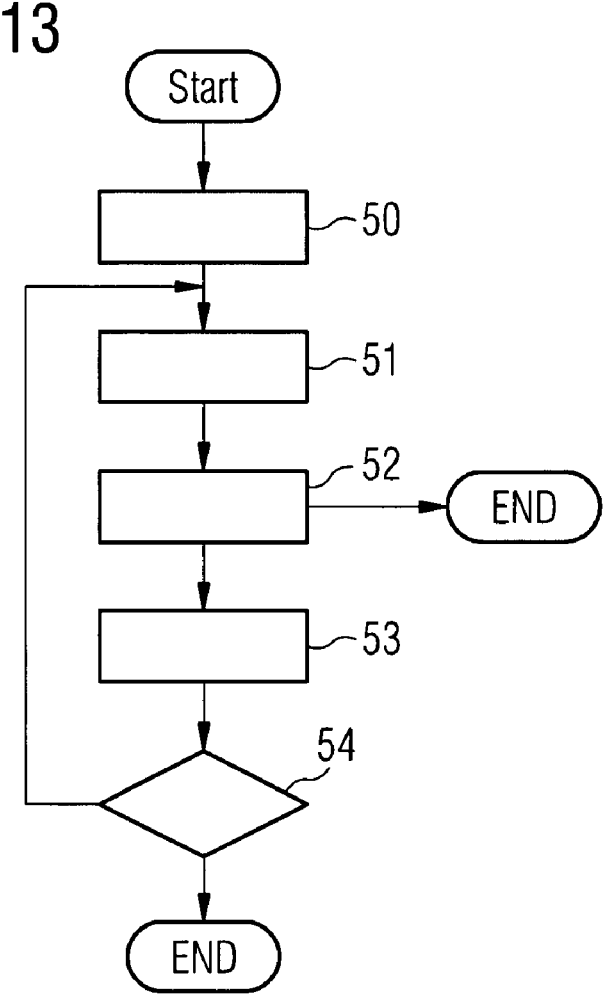
FIG. 13 is a flowchart which illustrates the sequence of steps performed with the correction method.

A flowchart is shown in FIG. 13 to illustrate the sequence of steps executed in the method.

In the flowchart shown in FIG. 13 to illustrate the scattered radiation correction method, start values are first assigned to the variables for the primary radiation fractions by value assignment 50. Next, the implicit equation (#18) is solved 51. The solving 51 of the implicit equation (#18) yields the searched-for scattered radiation fractions as well as a value for the mass per unit area. With the scattered radiation fractions obtained, a correction 52 of the measured radiation intensities to the primary radiation fractions can be performed. The method for scattered radiation correction can thus be terminated already.

Since the implicit equation (#18) is based on assumptions concerning the dependence of the primary-to-scatter ratios of the mass per unit area, it can make sense to perform a correction 53 of the mass per unit area and, following a query 54, to start an iteration in which a further solution 51 of the implicit equation (#18) is performed. With the query 54 it is possible, for example, to check a deviation of the ratio c on which the implicit equation (#18) is based from that ratio c which would have to be applied in accordance with the mass per unit area obtained.

With the method for scattered radiation correction shown in FIG. 13, basically only the method steps 50 to 52 need to be performed. An iteration is not necessary in every case.

8. Advantages

The methods described here are characterized by a comparatively great simplicity.

Compared with the estimation methods as applied when measurement data recorded using only one energy spectrum is available, the methods have the advantage that they do not have to rely primarily on computing models and empirical data from a standard phantoms database, said data having been measured previously or simulated by means of Monte Carlo programs, but instead that they make use of the discrepancy between the data measured with different spectra directly for determining and correcting the scattered radiation.

Furthermore, the computational overhead for performing the methods is relatively low.

For global estimation of the average scattered radiation background intensity it suffices to use an average value of a suitable region of interest for the low—or higher-energy projection image in each case. The computational overhead comprises at a maximum three table accesses, where appropriate with interpolation, which have to be repeated with few two to three iterations.

The location dependence of the scattered radiation background can be registered by applying the computing procedure on a uniform coarse grid of regions of interest or sampling points on the detector and expanding the result by means of interpolation from the coarse grid to the original fine pixel grid.

Finally, the methods can be generalized and combined with more complex methods of the location-invariant or location-variant convolution methods type.

The methods described here are not limited to soft tissue, but can also be extended to material combinations such as soft tissue and bone.

It should be pointed out that features and characteristics that have been described in connection with a specific exemplary embodiment can also be combined with a different exemplary embodiment, except when this is excluded for reasons of compatibility.

Finally, it is pointed out that in the claims and in the description the singular includes the plural, except when something different emerges from the context. In particular when the indefinite article is used, both the singular and the plural are meant.

The invention claimed is:

1. A method for scattered radiation correction, comprising:
   generating radiations in different energy ranges;
   irradiating an examination object with the radiations;
   recording attenuation images of the examination object in the different energy ranges by detecting the irradiated radiations;
   determining secondary radiation fractions of the attenuation images caused by scatter from image values of the attenuation images in a correction image area which maps a region of the examination object with a homogeneous attenuation coefficient; and
   correcting the attenuation images recorded in the different energy ranges with regard to the secondary radiation fractions to primary radiation fractions generated by attenuations,
   wherein the secondary radiation fractions which are linked to the primary radiation fractions with an identical mass per unit area are identified in the correction image area when inverse primary radiation functions are evaluated.

2. The method as claimed in claim 1, wherein predetermined relationships between the primary radiation fractions and the secondary radiation fractions as a function of the mass per unit area are defined in the correction image area.

3. The method as claimed in claim 2, wherein predetermined ratios of the secondary radiation fractions to the primary radiation fractions as a function of the mass per unit area are evaluated in the correction image area.

4. The method as claimed in claim 3, wherein predetermined relationships between the ratios of the secondary radiation fractions to the primary radiation fractions as a function of the mass per unit area are evaluated.

5. The method as claimed in claim 4, wherein a constant value is determined for a ratio of the ratios of the secondary radiation fractions to the primary radiation fractions.

6. The method as claimed in claim 4, wherein an attenuation image for a secondary radiation fraction and a further attenuation image for a further secondary radiation fraction each linked to a primary radiation fraction and a further primary radiation fraction with an identical mass per unit area are identified in the correction image area when an inverse primary radiation function is evaluated in each case.

7. The method as claimed in claim 2, wherein the mass per unit area is determined after the secondary radiation fractions are identified and the secondary radiation fractions are identified again taking into account the previously determined mass per unit area.

8. The method as claimed in claim 1, wherein the correction image area comprises an individual pixel of the attenuation images.

9. The method as claimed in claim 1, wherein the image values of the attenuation images are averaged and the secondary radiation fractions are determined based on the averaged image values in the correction image area.

10. The method as claimed in claim 1, wherein a secondary radiation intensity is determined from the secondary radiation fraction in the correction image area and is subtracted from image values outside the correction image area.

11. The method as claimed in claim 1, wherein a secondary radiation intensity is calculated from the secondary radiation fraction in the correction image area and a correction factor for correcting image values outside the correction image area is determined based on the secondary radiation intensity.

12. The method as claimed in claim 1, wherein the secondary radiation fractions are determined in the correction image area of a grid extending over the attenuation images.

13. The method as claimed in claim 12, wherein image values outside the correction image area are corrected as a function of the secondary radiation fractions determined in adjacent correction image areas.

14. The method as claimed in claim 1, wherein secondary radiation fractions in a correction image area with an inhomogeneous attenuation coefficient are determined by approximation based on the secondary radiation fractions in the correction image area with the homogeneous attenuation coefficient.

15. The method as claimed in claim 14, wherein the secondary radiation fractions in the correction image area with the inhomogeneous attenuation coefficient are determined by interpolating or extrapolating the secondary radiation fractions in the correction image area with the homogeneous attenuation coefficient adjacent to the correction image area with the inhomogeneous attenuation coefficient.

16. The method as claimed in claim 15, wherein the correction image area with the inhomogeneous attenuation coefficient is a region of a patient comprising bone of the patient or an implant which is not manufactured from hydrocarbon-based plastics.

17. The method as claimed in claim 1, wherein the correction image area with the homogeneous attenuation coefficient is a region of a patient comprising soft tissue or hydrocarbon-based plastics.

18. A device for recording attenuation images of an examination object, comprising:
  a radiation source that generates radiations in different energy ranges for irradiating the examination object;
  a detector that records the attenuation images in the different energy ranges; and
  an evaluation unit connected to the detector that:
    determines secondary radiation fractions of the attenuation images caused by scatter from image values of the attenuation images in a correction image area which maps a region of the examination object with a homogeneous attenuation coefficient, and
    corrects the attenuation images with regard to the secondary radiation fractions to primary radiation fractions generated by attenuations,
  wherein the secondary radiation fractions which are linked to the primary radiation fractions with an identical mass per unit area for the correction image area are identified when inverse primary radiation functions are evaluated.

* * * * *